United States Patent [19]

Lindley et al.

[11] Patent Number: 4,683,340
[45] Date of Patent: Jul. 28, 1987

[54] BIS(BENZILYLOXY) COMPOUNDS

[75] Inventors: Patricia M. Lindley, Springfield, Va.; Bruce A. Reinhardt, New Carlisle; Fred E. Arnold, Centerville, both of Ohio

[73] Assignee: The United States of America as represented by the Secretary of the Air Force, Washington, D.C.

[21] Appl. No.: 916,964

[22] Filed: Oct. 8, 1986

[51] Int. Cl.⁴ .......................................... C07C 49/794
[52] U.S. Cl. ...................................... 568/331; 528/125
[58] Field of Search ......................... 568/331; 528/125

[56] References Cited

U.S. PATENT DOCUMENTS

| | | | |
|---|---|---|---|
| 3,876,614 | 4/1975 | Hedberg et al. | 260/47 UA |
| 4,098,825 | 7/1978 | Arnold et al. | 568/331 |
| 4,147,728 | 4/1979 | Rabilloud et al. | 568/331 |
| 4,375,536 | 3/1983 | Hergenrother | 528/125 |

Primary Examiner—James H. Reamer
Attorney, Agent, or Firm—Charles E. Bricker; Donald J. Singer

[57] ABSTRACT

Bis(benzilyloxy) compounds having the general formula

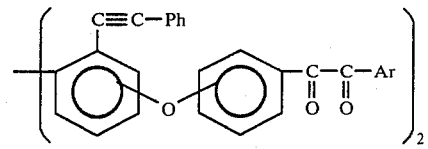

wherein Ph is $-C_6H_5$ and Ar is Ph, $-C_6H_4Br$, $-C_6H_4CH_3$ or $-C_6H_4C_2H_5$. These compounds can be reacted with bis(o-diamines) to form polyquinoxalines which can be converted to thermally stable compositions by non-volatile, intramolecular cyclization.

4 Claims, No Drawings

BIS(BENZILYLOXY) COMPOUNDS

RIGHTS OF THE GOVERNMENT

The invention described herein may be manufactured and used by or for the Government of the United States for all governmental purposes without the payment of any royalty.

BACKGROUND OF THE INVENTION

This invention relates to quinoxaline polymers having pendant phenylethynyl groups.

During the past several years, polymeric materials have been developed that possess heat resistance and strength properties found previously only in metals. In addition, the polymers are much lighter than metals, an important advantage where weight is a factor as in modern high-speed aerospace applications. By utilizing structure-property relationships, such as aromatic rings for thermal stability and aromatic-heterocyclic rings for adhesive and cohesive characteristics, it is possible to tailor polymer structures to provide desired end-use properties, such as strength, adhesiveness, elasticity, solvent-resistance, etc. While it may thus be possible to provide a suitable polymer system for a given application, the problem of processing the polymer into an end-use item must also be considered. The processing problem has probably been the most restrictive factor in limiting the use of high temperature resistant polymers.

To process a polymer into a composite structure, it is necessary to cause the polymer to flow in order to impregnate the reinforcing substrate and mold to the desired form. The lower the softening point (Tg) or the melting point (Tm) of a polymer, the easier it is to cause the polymer to flow. In general, a softening point of about 200° C. or below is most desirable. While a composite fabricated with a polymer having a softening point of 200° C. is suitable for use at 30° C, it can soften and lose its strength at temperatures approaching 200° C. To render the composite suitable for use at temperatures greater than 200° C., a method is required for subsequently raising the softening point of the polymer higher than the desired maximum use temperature. The conventional method of raising polymer softening points is to cure the polymer by joining new chemical bonds or crosslinks between polymer chains. In the curing method most widely employed, a trifunctional monomer is used in the polymer synthesis to provide crosslinking sites along the polymer backbone. This method often leads to branching and gelation during synthesis or storage of prepreg solutions. Other methods for accomplishing crosslinking include radiation, addition of a free radical source, incorporation of a pendant group which can react thermally or chemically, and thermal scission of C—H bonds in the polymer backbone.

There are three major disadvantages to the crosslinking method of cure. One disadvantage results from the evolution of volatiles from any type of cure in which a condensation reaction is used. Because of the volatiles evolution, voids are formed by entrapped gases, effectively weakening the composite structure. A second disadvantage derives from the brittleness which is inherent in a three-dimensional network. The third disadvantage lies in the fact that the softening point is raised only as high as the cure temperature because of "freezing in" of the reactive sites when the polymer softening point reaches the cure temperature. In other words, the polymer begins to soften as the use temperature approaches the cure temperature.

It is an object of this invention to provide a monomers which can be employed to provide polyquinoxalines which can be converted to thermally stable compositions by non-volatile, intramolecular cyclization.

Other objects and advantages of the present invention will become apparent to those skilled in the art upon consideration of the accompanying disclosure.

SUMMARY OF THE INVENTION

In accordance with the present invention there is provided a monomer having the general formula:

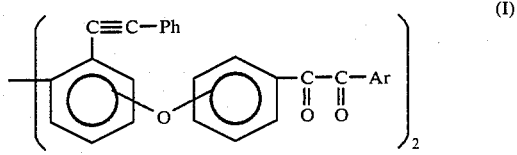

wherein Ph is —$C_6H_5$ and Ar is Ph, —$C_6H_4Br$, —$C_6H_4CH_3$ or —$C_6H_4C_2H_5$.

This monomer may be reacted with a bis-(o-diamine) to provide a quinoxaline polymer which consists essentially of repeating units of the general formula:

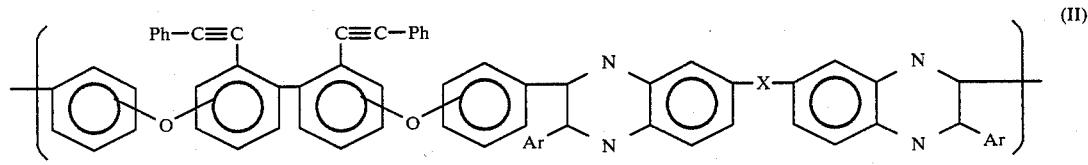

wherein X is a single bond, —O—, —S— or —$SO_2$—, and Ph and Ar are as described above.

There are at least two, and generally at least four of the recurring units in the polymers. In general, the number of recurring units is such that the polymers have an inherent viscosity about 0.50 to 1.5 dl/g in m-cresol at 30° C.

The preparation of the bis(benzilyloxy) monomer (I) is illustrated by the following reactions:

(a) 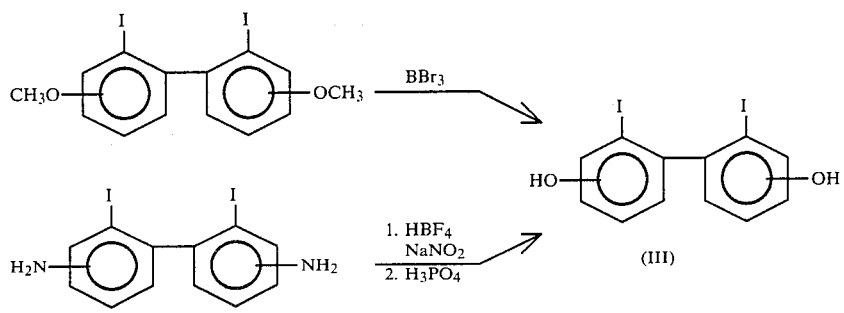

(b)

(c) 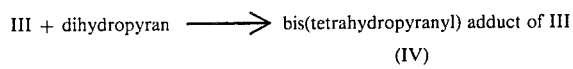

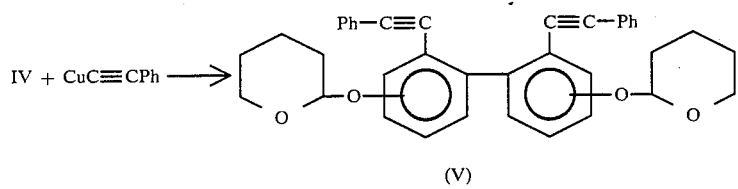

(d) 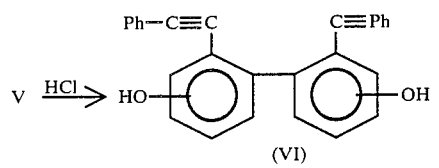

(e) 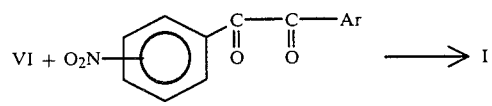

The above reactions are further described hereinafter in Example I.

Preparation of the polymer (II) is illustrated by the following equation:

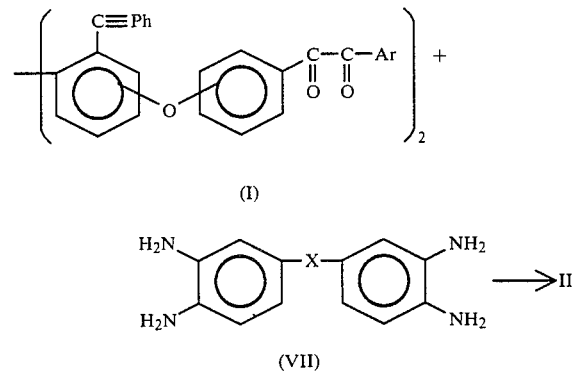

The reaction illustrated by the foregoing equation is conducted by combining stoichiometric quantities of II and III in an inert atmosphere, employing an aprotic solvent as the reaction medium at a concentration of about 5 to 30 w/v percent. Examples of inert gases that can be used include nitrogen, argon, helium, and the like. Examples of suitable aprotic solvents include m-cresol, dimethyl formamide, dimthyl acetamide, hexamethyl phosphoramide, tetramethyl urea, dimethyl sulfoxide, tetrachloroethylene, trichloroethylene, chloroform, and the like. It is generally preferred to utilize m-cresol as the reaction medium. The reaction is usually conducted at a temperature ranging from about room temperature to 100° C. for a period of about 1 to 96 hours. It is critical that the temperature does not exceed 100° C. in order to ensure that the acetylenic groups do not react prematurely. Upon completion of the reaction, the product is conveniently recovered by adding the reaction mixture to an alcohol, such as methanol, thereby precipitating the polymer from solution. After recovery of the polymer, as by filtration or decantation, it is washed with an alcohol and finally air dried or dried under reduced pressure. In order to purify the polymer further, the foregoing procedure may be repeated one or more times, i.e., dissolution of the dried polymer by adding the solution to an alcohol, separation of the precipitated polymer, and drying of the separated polymer.

In the synthesis of the quinoxaline polymers, the monomers are generally employed in equimolar amounts. While a small excess of one of the monomers is not detrimental to the condensation reaction, a considerable excess of one of the reactants results in the production of lower molecular weight products.

The bis(o-diamines) employed in the synthesis are well known compounds that are described in the literature. Examples of bis(o-diamines) include 3,3',4,4'-tetraaminobiphenyl, 3,3',4,4'-tetraminodiphenylether, 3,3'4,4'-tetraaminodiphenylsulfide and 3,3',4,4'-tetraaminodiphenylsulfone.

The bis(benzilyloxy) monomer, which is characterized by having pendant phenylethynyl groups, is a new compound. The presence of these pendant groups on the quinoxaline polymer chain provides an internal crosslinking mechanism whereby the fusible polymer can be cured by internal cyclization to an infusible polymer.

Curing of the quinoxaline polymers is accomplished by heating them in an inert atmosphere at a temperature ranging from about 240° to 300° C. A heating period of from about 1 to 2 hours is usually sufficient to obtain a complete cure although longer times, e.g., up to 24 hours, can be used. In the curing operation, cyclization of the pendant phenylethynyl moieties occurs, resulting in a cured polymer containing a benzotriphenylene structure as follows:

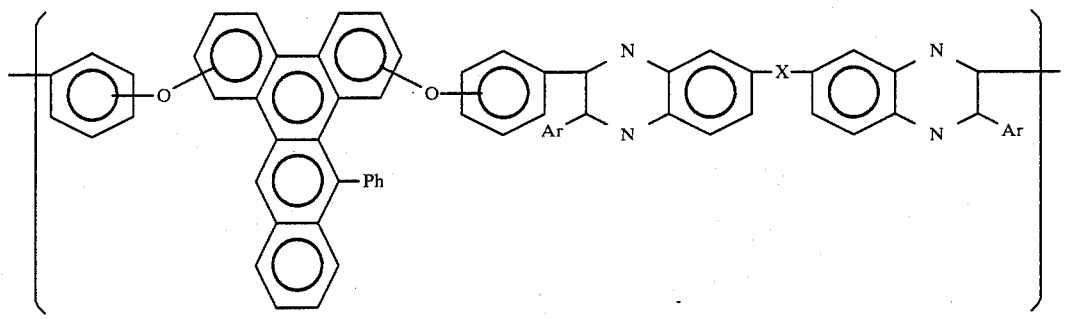

wherein X, Ar and Ph are as previously described.

The following examples illustrate the invention:

EXAMPLE I

Preparation of 4,4'-bis(benzilyloxy)-2,2'-bis(phenylethynyl)biphenyl (II)

a. 4,4'-dihydroxy-2,2'-diiodobiphenyl (IV)

Glacial acetic acid (200 ml) and 2,2'-diiodobenzidine (20.0 g, 49 mmol) were stirred at room temperature for 20 minutes, and then 100 ml 48% tetrafluoroboric acid was added to the solution. After 30 minutes, the acidic solution was cooled to −5° C., and a sodium nitrite solution (7.2 g NaNO$_2$ in 80 ml water) was slowly added to maintain the temperature below 0° C. The reaction was stirred for 1 hour at 0° C., and the precipitate which formed was filtered and dried for 18 hours under vacuum. The dried product was added over a period of 1 hour to a solution of 2 L water containing 30 ml 85% phosphoric acid at 75° C.

Nitrogen was evolved, and heating continued until the evolution of gas was complete (approx. 30 min.). The reaction was cooled to room temperature, the orange product filtered, and recrystallized from 3:1 water:ethanol. A white crystalline product, II, mp 171°–172° C., was collected in 25% yield.

Analysis Calc'd for $C_{12}H_8I_2O_2$: C, 32.88; H, 1.83; I, 57.99; Found: C, 33.10; H, 1.76; I, 57.64.

b. bis(tetrahydropyranyl) adduct of 4,4'-dihydroxy-2,2'-diiomodobiphenyl (V)

A mixture of IV (10.0 g, 22.8 mmol) and dihydropyran (12.5 ml, 137 mmol) was cooled to 10° C. A small crystal of p-toluenesulfonic acid was added to the reaction and the cooling bath was removed. As the reaction neared room temperature, an exotherm was noted which caused all of the diol to dissolve. After stirring for 1 hour, the solution was diluted with 100 ml methylene chloride, washed with 10% sodium hydroxide solution and water, and then dried with magnesium sulfate. The volume of the organic phase was reduced to 30 ml and diluted with 200 ml petroleum ether. A white precipitate formed upon stirring of the solution. The precipitate was collected and dried to give a 90% yield of III, mp 105°–106° C.

Analysis Calc'd for $C_{22}H_{24}I_2O_4$: C, 43,60; H, 4.04; I, 41,86; Found: C, 43.60; H, 3.96; I, 41.79.

c. phenylation of adduct V

A mixture of V (5.0 g, 8.25 mmol), copper phenylacetylide (3.39 g, 20.6 mmol) and 100 ml pyridine was purged with nitrogen for 15 minutes and then heated to reflux for 48 hours. After cooling to room temperature, pyridine was removed from the reaction mixture, and the residue was extracted with 2×300 ml hot benzene.

The benzene solutions were filtered hot and then dried thoroughly under vacuum to yield a yellow solid. The solid was chromatographed on a short (5 cm×20 cm) column using 2:1 petroleum ether; ether as eluant. The product fractions were evaporated to dryness to yield 50% of VI, mp 135°–137° C.

Analysis Calc'd for $C_{38}H_{34}D_4$: C, 82.3; H, 6.14; Found: C, 81.95; H, 6.20.

d. 4,4'-dihydroxy-2,2'-bis(phenylethynyl)biphenyl (VII)

To a mixture of 250 ml methanol and VI (5.0 g, 9.0 mmol) was added 2 ml conc. HCl. After 1 hour, all of VI was dissolved and TLC, eluted in 1:1 petroleum ether:ether, indicated that all protecting groups had been cleaved to the diol. The solution was neutralized with sodium bicarbonate, filtered, and evaporated to dryness. The residue was recrystallized from toluene to give a 90% yield of VII, mp 187° C.

Analysis Calc'd for $C_{23}H_{18}O_2$: C, 87.02; H, 4.69; Found: C, 86.90; H, 4.98.

e. 4,4'-bis(benzilyloxy)-2,2'-bis(phenylethynyl)biphenyl (II)

A mixture of VII (2.5 g, 6.48 mmol), 4-nitrobenzil (3.47 g, 13.60 mmol), and 65 ml dry DMSO was purged with nitrogen for 15 minutes. After the yellow solution was heated to 60° C., anhydrous potassium carbonate (2.3 g, 16.19 mmol) was added and the solution immediately became dark purple in color. Heating continued for 24 hours, then the reaction was cooled to room temperature and precipitated into 300 ml 10% HCl. The yellow product was filtered, dried, and chromatographed using 1:1 petroleum ether:methylene chloride as eluent. Product fractions were evaporated to give a 63% yield of VI, an amorphous yellow solid.

Analysis Calc'd for $C_{56}H_{34}O_6$: C, 83.77; H, 4.25; Found: C, 83.87; H, 4.27.

EXAMPLE II

Preparation of 5,5'-dihydroxy-2,2'-diiodobiphenyl (IV)

A flask containing 5,5'-dimethoxy-2,2'-diiodobiphenyl (10.0 g, 21 mmol) was cooled to −76° C. in dry ice/acetone. A 1.0M solution of boron tribromide in methylene chloride (64 ml, 64 mmol) was added via syringe to the cold substrate. The ice bath was removed and the reaction allowed to reach room temperature. After 18 hours, the solution was added slowly to 1 L of water. The aqueous mixture was stirred for 2 hours, and the white solid which formed was filtered, washed with water, and dried to give I, which melted at 181°–182° C., in 85% yield.

Analysis Calc'd for $C_{12}H_8I_2O_2$: C, 32.88; H, 1.83; I, 57.99; Found: C, 32.75; H, 1.90; I, 58.11.

EXAMPLE III

A mixture of 4,4'-bis(benzilyloxy)-2,2'-bis(phenylethynyl)-biphenyl (0.534 g, 0.6658 mmol) and 3,3'-diaminobenzidine (0.1427 g, 0.6658 mmol) was dissolved in 6 ml chloroform and purged with nitrogen for 15 minutes. Purified m-cresol (6 ml was purged with nitrogen and then added to the monomer mixture. The reaction mixture became dark red in color and became too viscous for stirring after 20 hours. The solution was heated to 60° C. for 4 hours, then cooled to room temperature and diluted with 40 ml chloroform. The polymer was reprecipitated into methanol. After drying under reduced pressure at room temperature, a 95% yield was obtained. The polymer exhibited an inherent viscosity of 0.91 in m-cresol.

Analysis Calc'd for $C_{68}H_{40}N_4O_2$: C, 86.3; H, 4.2; N, 5.9; Found: C, 85.44; H, 4.34; N, 6.01.

Various modifications and alterations may be made without departing from the spirit of the invention or the scope of the appended claims.

We claim:

1. A bis(benzilyloxy) compound of the general formula:

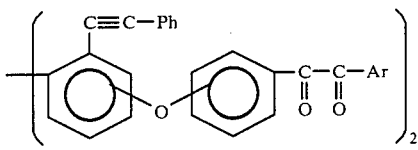

wherein Ph is —$C_6H_5$ and Ar is Ph, —$C_6H_4Br$, —$C_6H_4CH_3$ or —$C_6H_4C_2H_5$.

2. The compound of claim 1 wherein Ar is —$C_6H_5$.

3. In accordance with claim 2, the compound 4,4'-bis(benzylyloxy)-2,2'-bis(phenylethynyl)biphenyl.

4. In accordance with claim 2, the compound 5,5'-bis(benzilyloxy)-2,2'-bis(phenylethynyl)biphenyl.

* * * * *